United States Patent [19]

Cantaluppi

[11] 4,045,369

[45] Aug. 30, 1977

[54] SILVER-BASED CATALYTIC COMPOSITION FOR THE OXIDATION OF ETHYLENE TO ETHYLENE OXIDE AND METHANOL TO FORMALDEHYDE

[75] Inventor: Angelo Cantaluppi, Milan, Italy

[73] Assignee: S.A.E.S. Getters S.p.A., Milan, Italy

[21] Appl. No.: 670,954

[22] Filed: Mar. 26, 1976

[30] Foreign Application Priority Data

Apr. 2, 1975 Italy ............................ 21923/75
Mar. 11, 1976 Italy ............................ 21076/76

[51] Int. Cl.² .................. B01J 21/04; B01J 21/08; B01J 23/08; B01J 23/50
[52] U.S. Cl. .................................. 252/432; 252/438; 252/443; 252/455 R; 252/463; 260/348.35

[58] Field of Search ............... 252/463, 432, 438, 443, 252/455 R; 260/348.5 R

[56] References Cited

U.S. PATENT DOCUMENTS

| 3,420,784 | 1/1969 | Keith et al. .................. 252/463 X |
| 3,960,775 | 6/1976 | Piccinini et al. .................. 252/463 |

*Primary Examiner*—W. J. Shine
*Attorney, Agent, or Firm*—Littlepage, Quaintance, Murphy, Richardson & Webner

[57] ABSTRACT

A catalytic composition having up to 10% barium, strontium and/or calcium, up to 8% indium, balance silver useful in oxidation reactions.

13 Claims, No Drawings

SILVER-BASED CATALYTIC COMPOSITION FOR THE OXIDATION OF ETHYLENE TO ETHYLENE OXIDE AND METHANOL TO FORMALDEHYDE

BACKGROUND OF THE INVENTION

1. Field of the Invention

The present invention relates to a silver-based catalytic composition suitable for use in processes for the oxidation of organic compounds, particularly for the oxidation of ethylene to ethylene oxide and of methanol to formaldehyde. Also, according to another aspect, the present invention relates to a process for the oxidation of ethylene to ethylene oxide and the process for the oxidation of methanol to formaldehyde.

2. Description of the prior art

Silver has been known for some time as a catalyst in the oxidation of ethylene to ethylene oxide and in the oxidation of methanol to formaldehyde. Variable amounts of other minor ingredients are usually used with the silver with the scope of increasing the catalytic efficiency. Examples of such additional materials include: copper, barium, the alkaline earth metals, iron, manganese, cadmium, zirconium, aluminum, amongst others, both singly and in combination. There are also known silver-based catalytic compositions which include small quantities of an alkaline earth metal and a metal chosen from the third group of the Periodic Table of Elements. In fact, U.S. Pat. No. 3,461,140 describes catalytic compositions useful in the manufacture of ethylene oxide consisting of silver, an alkaline earth metal (particularly barium and calcium) and aluminum and/or boron. This patent, however, does not consider the possibility of using as a metal of the third group a metal belonging to Group IIIa of the periodic system of elements, in particular, indium. In fact, in U.S. Pat.No. 3,461,140 only aluminum is exemplified.

Prior catalytic compositions of the type described above exhibit several disadvantages. For example, apart from containing toxic materials, they have a surface area to mass ratio which decreases with time at the temperatures normally used in the above-described oxidation processes with a corresponding decrease of catalytic activity. In order to keep the productivity of the plant constant to overcome the decreased catalytic activity, one must increase the operating temperature. This has obvious disadvantages such as increased production costs and decrease in life of the catalyst.

SUMMARY OF THE INVENTION

It is, therefore, an object of the present invention to provide an improved catalytic composition substantially free of one of more of disadvantages of prior compositions.

A further object of the present invention is that of providing an improved catalytic composition of reduced toxicity.

Another object of the present invention is that of providing an improved catalytic composition whose exposed surface area to mass ratio does not decrease during use as much as that of prior compositions.

Yet another object of the present invention is that of providing a method of producing such improved catalytic compositions.

Yet a further object of the present invention is that of providing an improved process for producing ethylene oxide by the oxidation of ethylene using a catalyst of the present invention.

A further object is that of providing an improved process for the production of formaldehyde by the oxidation of methanol using a catalytic composition according to the present invention.

Further objects and advantages of the present invention will become evident to the experts in the art from the following description.

According to the present invention, there is provided a catalytic composition based on silver comprising from 0.001 to 10% based on the weight of silver of a metal chosen from the group consisting of strontium, calcium, and preferably barium; from 0.001 to 8% based on the weight of silver of indium, the remainder of the composition consisting essentially of silver.

DESCRIPTION OF THE PREFERRED EMBODIMENTS

It has been found that, if it is desired that the temperatures at which the oxidation reaction of ethylene is carried out be essentially the same as those of the known processes (i.e. between about 200° and 300° C), the catalytic compositions of the present invention preferably comprise:

A — from 0.001 to 5% based on the weight of silver of a metal chosen from the group comprising barium, strontium, and calcium, B — from 0.01 to 2% based on the weight of silver of indium, C — the remainder consisting essentially of silver.

A particularly preferred catalytic composition of this type comprises:

A — from 0.01 to 2% of barium based on the weight of silver,

B — from 0.05 to 0.5% based on the weight of silver of indium,

C — the balance consisting essentially of silver.

An even more preferred catalytic composition of this type comprises:

A — from 0.1 to 2% of barium based on the weight of silver,

B — from 0.05 to 0.5% based on the weight of silver of indium,

C — the balance consisting essentially of silver.

It has also been surprisingly found that temperatures lower than 200° C, for instance between about 100° and 180° C, can be advantageously employed in the oxidation of ethylene to ethylene oxide, if the following catalytic composition is used, which comprises:

A — from 5 to 6% based on the weight of silver of a metal chosen for the group comprising barium, strontium and calcium;

B — from 2.5 to 5% based on the weight of silver of indium;

C — the balance consisting essentially of silver.

Of the barium, strontium and calcium metals, barium is that preferred as it produces the best results. This component can be present in the form of a halide, an oxide or a carbonate. The preferable halides are chlorides or bromides. The most preferred form is the oxide.

The indium is preferably present as the oxide, hydroxide, or halide.

The remaining part of the composition consists essentially of silver and is preferably free from toxic materials. However, additional ingredients can be present in an amount which does not negatively influence the new and important characteristics of the catalytic composition according to the invention. These inert ingredients can be present in weight amounts which reach or even supersede 10%.

The metals of Group Ia, that is lithium, sodium, potassium, rubidium and caesium can be present in amounts up to 5%. The metals of Group IIIb, scandium, yttrium and lanthanum can be present in amounts up to 1%. The elements of Groups IVa, Va, VIa and VII can also be present in amounts up to 1%. Metals of Group Ib such as copper and gold can be present in amounts up to 5% and preferably between 0.1 and 1%. Metals of Group IIb such as zinc and cadmium can be present in amounts up to 2%. Mercury, thallium, phosphorous and arsenic are poisons and should be absent. However, their presence can be tolerated in amounts up to 1%. The metals of Group IIIa apart from indium which constitutes the critical component of the catalytic composition of the present invention do not influence negatively the catalytic composition and can be present in amounts up to 10%. The elements of Group IVb can be present in amounts up to 1%. Metals of Group Va such as antimony and bismuth can be present in amounts up to 1%. The halogens are poisonous if present in amounts greater than about 1%. However, they can increase the catalytic activity if present in small quantities less than 1% as is well known in the art. The halogens can be present in the form of halides as previously described.

The catalytic compositions of the present invention can be produced by any process in which the components are brought into intimate contact with each other within the concentration ranges previously described. However, the catalytic compositions of the present invention are preferably produced by co-precipitating the silver and the indium as In(OH)$_3$ followed by contacting with the compound of barium, strontium and/or calcium. According to one embodiment of the present invention, the co-precipitation can take place in the presence of hard particles to be used later according to the description in Italian Pat. No. 960,613.

Alternatively, the silver and indium hydroxide can be precipitated without the presence of hard particles and then used as soft particles according to the teachings of Italian Pat. No. 960,613. The hard particles must not inhibit the catalytic reaction. Non-limiting examples of suitable hard particles comprise among others silicon nitride, boron nitride, silicon carbide, silica and alumina, the last being preferred. The alumina can be that sold by the firm Norton with the tradename "ALUNDUM". The ALUNDUM should have a purity of about 99.6% and a particle size between 20 and 300 microns, and preferably from 40 to 100 microns. The weight ratio between hard particles and catalytic particles is generally between 1:20 and 4:1 and preferably between 1:10 and 1:1.

The catalytic compositions of the present invention can be used on supports as is well known in the art of catalysis. Non-limiting examples of suitable supports include among others alumina, diatomaceous earth, kieselguhr, silicon carbide, silicon nitride, boron nitride and silica. The preferred supports have a surface area to mass ratio between 0.03 and 10 m$^2$/g. However, even supports which do not fall within this interval are useful. The support can be in any physical form, as for example, pills, rings, or pellets.

The catalytic compositions of the present invention can be used in place of known catalytic compositions without substantially changing the process conditions for the production of ethylene oxide or formaldehyde. As is well known in the art, ethylene oxide is generally produced by contacting ethylene and oxygen preferably at 200° to 300° C, at a pressure of about 1 to 30 atmospheres using gas ratios such that the resultant mixture is non-explosive. As is well known in the art, methanol is generally oxidized to formaldehyde with air or oxygen-containing gases at temperatures of 0° to 500° C and preferably 100° to 400° C. Certain catalytic compositions of the present invention permit to effectively catalyze the oxidation reaction of ethylene at temperatures lower than those of the known processes, i.e. even at temperatures as low as 100°-180° C, e.g. at 140° C.

The invention will now be further illustrated with the following examples in which all parts and percentages are in weight unless otherwise stated. These non-limitative examples illustrate certain practical realization and are intended to show the experts in the art the best way of practicing the invention. Examples 1 to 3 refer to catalytic compositions according to the prior art and are present for comparative purposes with other examples which illustrate the use of catalytic compositions according to the present invention.

The catalysts are used in the production of ethylene oxide and formaldehyde. The composition of the various catalysts, the operating conditions of the process of oxidation of ethylene and the parameters of yield, selectivity and conversion are indicated in the Table.

EXAMPLE 1

The following example shows the preparation of a known catalyst for comparison purposes. In a glass reactor vessel of 1500 ml provided with a stirrer, thermometer and a water-cooling jacket are placed 56.6 grams of silver nitrate, 700 ml of distilled water, 14.1 grams of alumina (purity 99.6, particle size 40 to 100 microns, type ALUNDUM from Norton S.p.A.) and 15.5 ml of formaldehyde of concentration equal to 40% w/v.

The whole is stirred and, maintaining the temperature below 20° C, there are slowly added drop-wise 93 ml of sodium hydroxide of concentration equal to 200 mg/ml.

Stirring is continued for 10 minutes after the end of the reaction and then the precipitated mass is filtered and washed carefully several times with distilled water until there are practically no more sodium ions.

The precipitate is washed with acetone and dried in an oven at 50° C.

The dried mass is placed in a 50 ml flask and 22.4 ml of Ba(OH)$_2$ solution containing 16.8 mg of barium per ml is added. The contents of the flask are evaporated rapidly to dryness in vacuum at 50° C in a rotating evaporator. The last traces of moisture are removed by treatment in a vacuum oven at 180° C for 6 hours. The dry catalyst is powdered carefully in a mortar and sieved, collecting the powder of grain-size less than 250 microns.

The resulting catalyst contains 30% by weight of ALUNDUM or a weight ratio between the catalyst and alumina of 7.3.

A quantity of catalyst containing 1.78 grams of silver is mechanically mixed with silicon carbide (grain-size 150 to 180 microns) until completely uniform obtaining a total volume of 30 ml.

The mixture is placed in a tubular glass reactor of internal diameter 16 millimeters immersed in a fluidized bath.

EXAMPLE 2

A known catalyst is prepared following the description of Example 1, but adding 0.4 ml of solution of beryllium nitrate containing 21 mg/ml of beryllium to the solution of $AgNO_3$.

This catalyst is also used for comparative purposes with catalysts of the present invention.

EXAMPLE 3

A known catalyst is prepared following the description of Example 1, but adding a solution of copper nitrate (6.8 ml) containing 31.78 mg/ml of copper to the solution of $AgNO_3$.

This catalyst is also used for comparison purposes with catalysts of the present invention.

EXAMPLE 4

A catalyst is prepared as described in Example 1 but adding to the solution of silver nitrate 1.2 ml of indium nitrate solution containing 32 milligrams of indium per ml. The catalytic composition obtained is illustrated in the Table.

EXAMPLES 5-6-7

The catalysts are prepared as described in the previous example, but varying the quantity of indium nitrate. The composition of the catalysts obtained is illustrated in the Table.

EXAMPLE 8

The catalyst is prepared as described in Example 5 varying the quantity of indium nitrate and not having the barium hydroxide.

EXAMPLE 9

The catalyst is prepared following the description of Example 4 adding to the solution of silver nitrate a solution of copper nitrate (6.8 ml) containing 31.78 mg/ml of copper.

EXAMPLES 10-11

These examples illustrate the stability of catalytic activity of the catalyst of the present invention placed on a support as indicated in Example 4.

A support covered with the catalytic composition as described in Example 1 was prepared. An amount of support containing 5 grams of silver was introduced into a tubular glass reactor having an internal diameter of 16 millimeters immersed in a fluidized bath for a total occupied volume of 30 ml. Even though severe experimental conditions were adopted, as indicated in the Table, the catalyst of the present invention is distinctly superior and, furthermore, is more stable with respect to known catalysts.

Example 11 is a continuation of Example 10.

Example 11 has been performed using a gas-phase moderator which has led to an increase in productivity of the catalyst of the present invention as indicated in the Table.

EXAMPLES 12-13

The catalytic composition of Example 4 without, however, the silicon carbide is applied to an aluminum support as described in Italian Pat. No. 960,613 in order to make a coated support.

This coated support is then formed into a catalytic cartridge as described in Italian Pat. No. 955,185.

Two separate experimental tests are performed inserting into a metallic reactor of internal diameter 32 millimeters 8 catalytic cartridges each time and allowing a gas mixture containing ethylene, oxygen and nitrogen to flow in order to test the catalytic activity of the structure.

The results are reported in the Table, together with the experimental conditions.

EXAMPLE 14

This example illustrates the stability of the surface area to mass ratio shown by catalytic compositions of the present invention.

The exposed surface area to mass ratio is measured on the catalytic composition of Example 4 and it is found to be equal to 2 $m^2/g$. This catalytic composition is subjected to an accelerated aging test at 500° C for 30 hours after which it is found that the previously mentioned ratio is still 2 $m^2/g$ not showing any decrease. The same test is performed on the catalytic composition of Example 2 which initially had a surface area to mass ratio of 3.3 $m^2/g$ and of 1.8 $m^2/g$ after aging at 500° C for 30 hours. Thus, the known comparative catalytic composition shows a reduction of 1.5 $m^2/g$ equal to a loss of 45% of its original surface area.

EXAMPLE 15

This example illustrates the synthesis of formaldehyde from methanol using a catalyst according to the present invention. The procedure of Example 12 is repeated using the catalytic composition of Example 4 except that the mixture of ethylene, oxygen and nitrogen is substituted by a mixture containing 10% methanol and 90% air with a space velocity of $7.000h^{-1}$ and a reaction temperature of 400° C. The resultant product is formaldehyde.

EXAMPLE 16

This example illustrates the activity of a catalytic composition particularly suited to carry out the oxidation of ethylene to ethylene oxide at low temperatures.

339.6 grams in the form of $AgNO_3 + 134.3$ cc of a solution of $In(NO_3)_3$ containing 64 L mg/cc In + 20.5 grams of $BaNO_3$ were added to 650 cc $H_2O$ till complete dissolution of the ingredients, thus obtaining solution (A).

825 grams of $Na_2CO_3.10H_2O$ were dissolved in 3500 cc distilled water and to this solution 124 mg NaCl were added, thus obtaining solution (B). Solution (B) was added under rapid stirring to solution (A) till complete precipitation of Ag, In and Ba carbonates was achieved. To the suspension thus obtained, 84 cc of a $CH_2O$ solution (40% w/v formaldehyde) were added dropwise under stirring. Stirring was continued until the silver was completely reduced. The suspension was filtered and washed with water till complete removal of Na ions, followed by drying in an air-oven at 150° C for 6 hours.

The powder thus obtained contained about 5% by weight of barium based on the silver weight, and about 4% by weight of indium based on the silver weight.

0.66 grams of this powder, after thorough mixing with 15 grams of carborundum, were charged into a tubular glass reactor (inner diameter: 16 millimeters) immersed in a fluidized bath, to test it in the oxidation reaction of ethylene. To this reactor a mixture of 64% by volume ethylene and 5% by volume oxygen, the balance being nitrogen, was fed at a feed rate of 60 m.moles ethylene/hour/gram Ag, obtaining ethylene oxide. The oxidation reaction temperature was 140° C. The selectivity was 75.39% with 0.5 m.moles of reacted ethylene/hour/gram Ag.

Even though the invention has been described in considerable detail with reference to certain preferred embodiments, it is understood that variations and modifications can be made without departing from the spirit and scope of the invention.

5. Catalytic composition according to claim 1 in which indium is present in an amount between 0.05 and 0.5% based on the weight of silver.

6. Catalytic composition according to claim 1 comprising:
   A. from 5 to 6% based on weight of silver of an oxide of a metal selected from a group consisting of barium, strontium and calcium,
   B. from 2.5 to 5% based on the weight of silver of an

TABLE

| EXAMPLES | 1 | 2 | 3 | 4 | 5 | 6 | 7 | 8 | 9 | 10 | 11 | 12 | 13 |
|---|---|---|---|---|---|---|---|---|---|---|---|---|---|
| According to the invention I Comparison C | C | C | C | I | I | I | I | I | I | I | I | I | I |
| Catalytic composition active part | | | | | | | | | | | | | |
| Ba % weight based on Ag | 1 | 1 | 1 | 1 | 1 | 1 | 1 | — | 1 | 1 | 1 | 1 | 1 |
| In % weight based on Ag | — | — | — | 0.1 | 0.25 | 1 | 0.05 | 0.05 | 0.1 | 0.1 | 0.1 | 0.1 | 0.1 |
| Cu % weight based on Ag | — | — | 0.6 | — | — | — | — | — | 0.6 | — | — | — | — |
| Be % weight based on Ag | — | 0.025 | — | — | — | — | — | — | — | — | — | — | — |
| Ag % weight based on Ag | 100 | 100 | 100 | 100 | 100 | 100 | 100 | 100 | 100 | 100 | 100 | 100 | 100 |
| Results | | | | | | | | | | | | | |
| Conversion % | 6 | 65.7 | 43.5 | 71.67 | 79.05 | 73 | 53.5 | 63.5 | 83.36 | 60.42 | 46.58 | 24.1 | 28.12 |
| Selectivity % | 71 | 29.9 | 46.8 | 54.01 | 24.3 | 13.6 | 48.76 | 48.61 | 55.1 | 49.414 | 65.91 | 65.51 | 68.41 |
| Yield % | 4.26 | 19.6 | 21.4 | 38.71 | 19.21 | 9.9 | 25.59 | 30.7 | 45.92 | 29.86 | 30.7 | 15.7 | 19.23 |
| Test time in h | 500 | 500 | 500 | 500 | 500 | 500 | 500 | 500 | 500 | 3000 | +500 | 500 | 1500 |
| Test temperature ° C | 250 | 250 | 250 | 250 | 250 | 250 | 250 | 250 | 250 | 320 | 320 | 250 | 260 |
| Absolute pressure m BAR | 1093.25 | 1093.25 | 1093.25 | 1093.25 | 1093.25 | 1093.25 | 1093.25 | 1093.25 | 1093.25 | 1066.58 | 1066.58 | 1173.24 | 1174 |
| Gas feed rate Nl/h | 21 | 21 | 21 | 21 | 21 | 21 | 21 | 21 | 21 | 42 | 42 | 1244 | 1244 |
| Feed composition | | | | | | | | | | | | | |
| Ethylene % Volume | 4 | 4 | 4 | 4 | 4 | 4 | 4 | 4 | 4 | 4 | 4 | 6.5 | 6.5 |
| Oxygen % Volume | 7.5 | 7.5 | 7.5 | 7.5 | 7.5 | 7.5 | 7.5 | 7.5 | 7.5 | 7.5 | 7.5 | 6.25 | 6.5 |
| Nitrogen % Volume | 88.5 | 88.5 | 88.5 | 88.5 | 88.5 | 88.5 | 88.5 | 88.5 | 88.5 | 88.5 | 88.5 | 87 | 87 |
| 1-2 dichloroethane ppm | — | — | — | — | — | — | — | — | — | — | 3 | — | 0.3-0 |
| Space velocity h$^{-1}$ | 663 | 700 | 700 | 700 | 700 | 700 | 700 | 700 | 700 | 1257 | 1257 | 7000 | 7000 |
| Productivity: | | | | | | | | | | | | | |
| g ethylene oxide/h.gAg | 0.037 | 0.172 | 0.188 | 0.340 | 0.169 | 0.087 | 0.225 | 0.265 | 0.403 | 0.175 | 0.180 | 0.433 | 0.430 |
| g ethylene oxide/h.l reactor | 2.22 | 10.215 | 11.153 | 20.174 | 10.012 | 5.159 | 13.34 | 16.00 | 23.93 | 29.167 | 29.99 | 141 | 172 |
| Quantity of Ag used (g) | 1.78 | 1.78 | 1.78 | 1.78 | 1.78 | 1.78 | 1.78 | 1.78 | 1.78 | 5 | 5 | 58 | 71 |

What is claimed is:

1. Catalytic composition based on silver comprising:
   A. from 0.001 to 10% based on the weight of silver of an oxide of a metal selected from the group consisting of barium, strontium and calcium,
   B. from 0.001 to 8% based on the weight of silver of an oxide of indium,
   C. the balance consisting essentially of silver.

2. Catalytic composition based on silver according to claim 1 comprising:
   A. from 0.001 to 5% based on the weight of silver of an oxide of a metal selected from the group consisting of barium, strontium and calcium,
   B. from 0.01 to 2% based on the weight of silver of an oxide of indium,
   C. the balance consisting essentially of silver.

3. Catalytic composition based on silver according to claim 1 comprising:
   A. from 0.1 to 2% of an oxide of barium based on the weight of silver,
   B. from 0.05 to 0.5% based on the weight of silver of an oxide of indium,
   C. the balance consisting essentially of silver.

4. Catalytic composition according to claim 1 in which Component A is present in an amount between 0.01 and 2% based on the weight of silver.

oxide of indium,
   C. the balance consisting essentially of silver.

7. Catalytic composition according to claim 6 comprising:
   A. 5% of barium based on the weight of silver,
   B. 4% of indium based on the weight of silver,
   C. the balance consisting essentially of silver.

8. Catalytic composition according to claim 1 deposited on a support having a surface area to mass ratio of 0.03 to 10 m²/g.

9. Catalytic composition according to claim 1 in mixture with a powdered material selected from the group consisting of silicon carbide, silicon nitride, boron nitride, silica and alumina.

10. Catalytic composition according to claim 9 in which the alumina is $Al_2O_3$ having a particle size between 40 microns and 100 microns.

11. Catalytic composition according to claim 10 in which the weight ratio between the catalytic material and $Al_2O_3$ is 7:3.

12. Catalytic composition according to claim 1 comprising furthermore copper.

13. Catalytic composition according to claim 12 in which the copper is present in an amount between 0.1 and 1% based on the weight of silver.

* * * * *